(12) United States Patent
Lavrijsen et al.

(10) Patent No.: US 10,687,966 B2
(45) Date of Patent: Jun. 23, 2020

(54) IMPLANT

(71) Applicant: Xeltis, BV, Eindhoven (NL)

(72) Inventors: Tom Lavrijsen, Eindhoven (NL); Anandkumar Nandakumar, The Hague (NL); Martijn Antonius Johannes Cox, Budel (NL); Franciscus Petrus Thomas Baaijens, Eindhoven (NL); Carolina Victoria Catharina Bouten, Eindhoven (NL); Anton Bosman, Eindhoven (NL); Tristan Mes, Eindhoven (NL); Patricia Yvonne Wilhelmina Dankers, Helmond (NL)

(73) Assignees: Xeltis AG, Zurich (CH); Technische Universiteit Eindhoven, Eindhoven (NL)

( * ) Notice: Subject to any disclaimer, the term of this patent is extended or adjusted under 35 U.S.C. 154(b) by 184 days.

(21) Appl. No.: 15/842,359

(22) Filed: Dec. 14, 2017

(65) Prior Publication Data
US 2018/0153717 A1 Jun. 7, 2018

Related U.S. Application Data

(63) Continuation of application No. 14/413,077, filed as application No. PCT/NL2013/050500 on Jul. 5, 2013, now Pat. No. 9,877,852.

(51) Int. Cl.
| A61F 2/86 | (2013.01) |
| A61F 2/91 | (2013.01) |
| A61L 27/18 | (2006.01) |
| A61L 27/50 | (2006.01) |
| A61L 27/56 | (2006.01) |
| A61F 2/00 | (2006.01) |
| A61F 2/24 | (2006.01) |
| A61L 27/54 | (2006.01) |
| A61L 27/58 | (2006.01) |

(52) U.S. Cl.
CPC .............. *A61F 2/86* (2013.01); *A61F 2/00* (2013.01); *A61F 2/24* (2013.01); *A61L 27/18* (2013.01); *A61L 27/507* (2013.01); *A61L 27/54* (2013.01); *A61L 27/56* (2013.01); *A61L 27/58* (2013.01); *A61L 2430/20* (2013.01)

(58) Field of Classification Search
CPC .................................... A61F 2/82; A61F 2/06
USPC ................................................ 623/1.15–1.54
See application file for complete search history.

(56) References Cited

U.S. PATENT DOCUMENTS

| | | | | |
|---|---|---|---|---|
| 7,968,026 | B1* | 6/2011 | Teoh | A61L 27/18 264/173.12 |
| 8,739,379 | B2* | 6/2014 | Pacetti | A61F 2/958 29/283.5 |
| 8,883,188 | B2* | 11/2014 | Dankers | A61L 27/34 424/426 |
| 9,107,739 | B2* | 8/2015 | Lelkes | A61F 2/06 |
| 2008/0183271 | A1* | 7/2008 | Frawley | A61F 2/958 623/1.11 |

(Continued)

FOREIGN PATENT DOCUMENTS

WO WO2007140964 12/2007

*Primary Examiner* — Suzette J Gherbi
(74) *Attorney, Agent, or Firm* — Lumen Patent Firm

(57) ABSTRACT

The disclosure lies in the field of regenerative medicine and relates to an implant having a matrix material, and a method for manufacturing an implant having matrix material. The disclosure further relates to a crimped implant.

21 Claims, 12 Drawing Sheets

(56) References Cited

U.S. PATENT DOCUMENTS

| | | | | |
|---|---|---|---|---|
| 2010/0122446 A1* | 5/2010 | Pacetti | A61F 2/958 | 29/282 |
| 2011/0250689 A1* | 10/2011 | Baaijens | D01D 5/0076 | 435/398 |
| 2012/0330437 A1* | 12/2012 | El-Kurdi | A61F 2/06 | 623/23.64 |
| 2013/0018454 A1* | 1/2013 | Lelkes | A61F 2/06 | 623/1.32 |
| 2013/0256375 A1* | 10/2013 | Shelton, IV | A61B 17/07207 | 227/176.1 |
| 2013/0331927 A1* | 12/2013 | Zheng | A61F 2/82 | 623/1.19 |
| 2014/0227338 A1* | 8/2014 | Ringeisen | C08J 9/28 | 424/426 |
| 2014/0238293 A1* | 8/2014 | Pacetti | A61F 2/958 | 118/44 |
| 2014/0277452 A1* | 9/2014 | Skaer | A61L 27/227 | 623/14.12 |
| 2014/0356445 A1* | 12/2014 | Little | A61K 9/0019 | 424/501 |
| 2015/0110753 A1* | 4/2015 | Wang | A61L 27/3604 | 424/93.7 |
| 2015/0273114 A1* | 10/2015 | Hauser | A61K 47/42 | 514/16.5 |
| 2015/0320908 A1* | 11/2015 | Hauser | A61L 27/22 | 514/773 |
| 2015/0359619 A1* | 12/2015 | Lelkes | A61F 2/06 | 264/465 |
| 2015/0367028 A1* | 12/2015 | Hauser | A61K 8/042 | 424/400 |

\* cited by examiner

Fig. 8 A
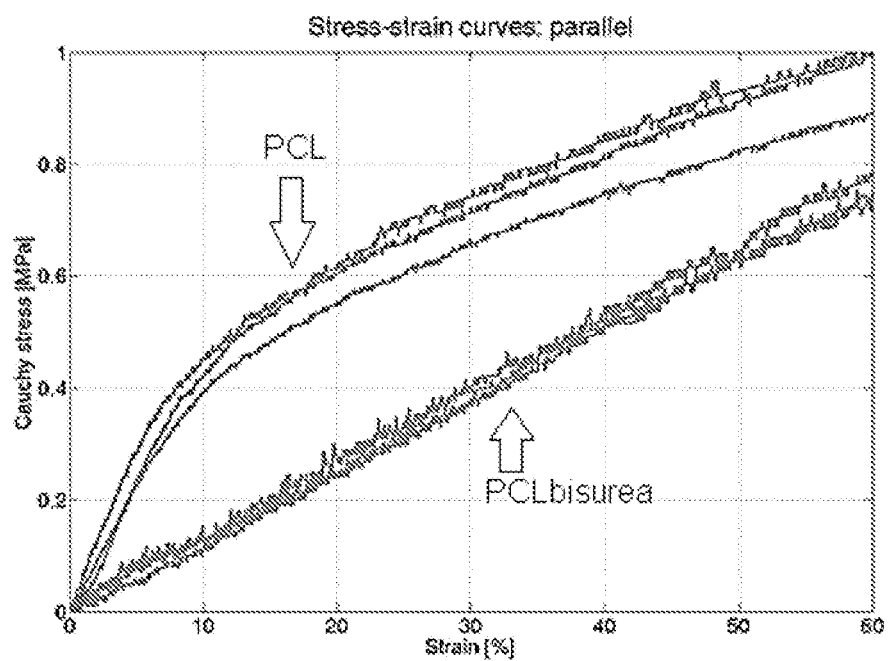
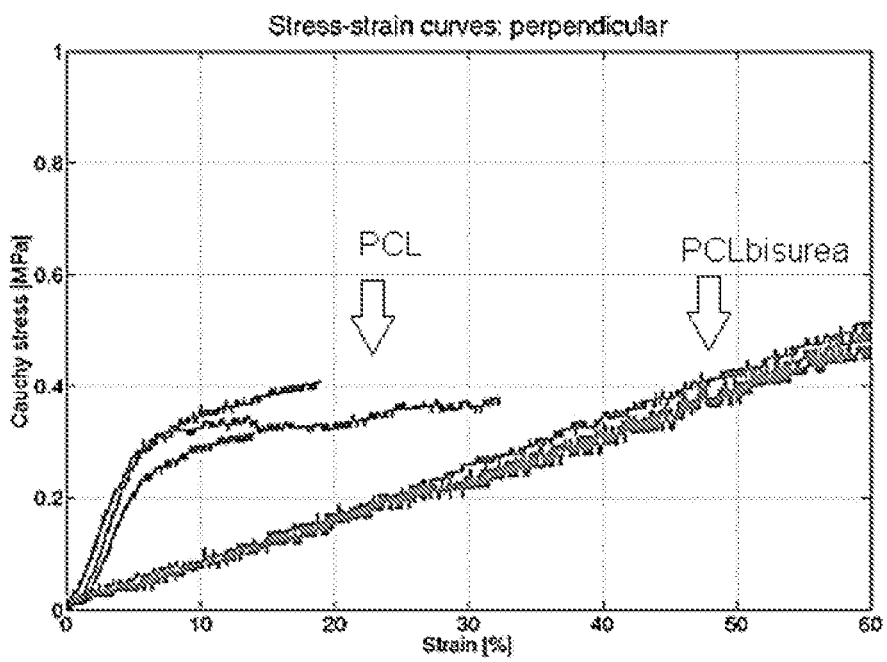
Fig. 8 B 1 day  7 days 8 weeks

IMPLANT

CROSS-REFERENCE TO RELATED APPLICATIONS

This application is a continuation of U.S. patent application Ser. No. 14/413,077 filed Jan. 6, 2015, which is incorporated herein by reference.

U.S. patent application Ser. No. 14/413,077 filed Jan. 6, 2015 is a 371 application of PCT PCT/NL2013/050500 filed Jul. 5, 2013.

PCT PCT/NL2013/050500 filed Jul. 5, 2013 claims the benefit from NL2009145 filed Jul. 6, 2012.

FIELD OF THE INVENTION

The invention relates to an implant comprising a matrix material, and a method for manufacturing an implant comprising matrix material. The disclosure further relates to a crimped implant.

BACKGROUND OF THE INVENTION

A relatively new field of medicine—since the early 1990s—is the field of Regenerative Medicine. Regenerative Medicine is the process of creating living and functional tissues to repair, replace, or restore tissue or organ structure and function lost due to age, disease, damage, or congenital defects. This field of medicine uses new methods including (stem) cell therapy, development of medical devices and tissue engineering.

Over recent years, continuous improvements in our healthcare have resulted in dramatic demographic changes, e.g. an increase in the average age of the population. These demographic changes are causing an increase in the prevalence of diseases associated with aging, such as cardiovascular diseases. Many of these diseases arise from the loss or dysfunction of specific cell types in the human body, leading to permanently damaged tissues and organs.

Cardiovascular diseases are one of the biggest causes of deaths worldwide. One way to treat at least some of these diseases is by tissue engineering. Tissue engineering can be used for the replacement of cardiovascular tissues, such as arteries and heart valves. Currently used cardiovascular substitutes encounter risks due to coagulation, infections, degeneration, and no growth possibilities. Tissue engineering uses patient's own cells and a biodegradable polymer scaffold to make autologous tissue that is able to grow, adapt and repair. To ensure proper cell and tissue growth, the scaffolds must be highly porous and match the mechanical properties of the tissue. Electrospinning is a technique that produces polymer nanofibers using a high voltage electrostatic field. It results in a highly porous material consisting of nanofibers that resembles the extra cellular matrix of the tissue. Tissue engineering can, for example, be used for coronary bypass grafts, heart valve replacements, AV shunts for dialysis patients.

In the field of surgery, minimal invasive surgery is preferred. However, tissue engineered constructs can often only be implanted via normal surgical procedures since the constructs cannot be compressed to a size sufficiently small to facilitate minimal invasive surgery. Some artificial heart valves can now be crimped to a diameter of 18 French (6 mm) to allow for implantation via a small peripheral incision (e.g. transfemoral or transjugular). However, many elderly patients in need of a replacement valves also suffer from stenotic and therefore narrowed arteries, which currently excludes them from the much-preferred minimal invasive surgery. A reduction of 1 or 2 French in crimpable diameter already means a significant increase in the number of treatable patients.

The technique of tissue engineering consists of constructing substitutes (e.g. biological substitutes) for diseased tissues. Tissue engineering makes use of natural or polymeric scaffolds that provide mechanical support and promote the re-growth of cells lost due to trauma or disease. A scaffold is a temporary structure used to support material (e.g. tissue) during the recovery thereof.

Polymeric scaffolds can be constructed from biocompatible, non-toxic polymers. The choice of polymer and the technique used to make the scaffold effects the mechanical properties exhibited by the scaffold.

In the publication of Bouten et al, Advanced Drug Delivery Reviews, 2011, vol. 63, pp 221-241 synthetic polymers have been demonstrated to be good substrates for valvular and vascular tissue engineering. For cardiac tissue engineering, the most commonly used biodegradable synthetic scaffold materials are polyglycolic acid (PGA), polylactic acid (PLA), polyhydroxybutyrates (PHB), ε-polycaprolactone (PCL) or their co-polymers. No functioning implants were disclosed using the described synthetic scaffold materials.

In the publication by Dankers et al in Nature Materials, 2005, Vol. 4, pp 568-574 solution cast polymer films comprising 2-ureido-4[1H]-pyrmidinone (UPy) polymers were shown to be non-toxic when studied in vivo. However, the use of UPy polymers as cardiovascular implant scaffolds was not shown.

In order to obtain a tissue engineered construct, a scaffold can be pre-seeded in vitro with the appropriate cells prior to implantation. In most cases, as the formation and the remodeling of the newly formed tissue proceeds, degradation of the scaffold should slowly and steadily take place, leaving only new healthy tissue behind By "degradation," it is meant the breakdown of the material into smaller parts, e.g. chemical compounds and/or elements that can be eliminated from the body by means of excretion in urine for example.

A drawback of growing a tissue construct in vitro is that the complete procedure including growing and implanting has to be conducted sterilely making it a costly and laborious procedure. In addition, regulatory guidelines on living tissues are complex, resulting in long and costly processes towards product approval.

Another option is to seed an implant with cells prior to implantation. This method requires the harvesting of cells from the subject to receive the implant, optionally growing the cells in vitro, and seeding the cells in the construct followed by implantation. This method has the same down sides as the previously described method.

SUMMARY OF THE INVENTION

It is an object of the present disclosure to provide for an implant which can be implanted via minimal invasive surgery.

It is an object of the present disclosure to provide for an implant which regenerates tissue in vivo.

It is further an object of the present disclosure to overcome one or more of the above-mentioned draw backs associated with the prior art.

One or more of the above objects have been reached by the embodiments of the present disclosure. The inventors have surprisingly found that the above objects are reached with an implant comprising one or more supramolecular compounds and wherein the matrix material comprises a fibrous network and having a porosity of at least 60%, preferably a porosity of between 70% and 90%.

The embodiments are illustrated in more detail in the following description and with reference to the drawings.

BRIEF DESCRIPTION OF THE DRAWINGS

FIG. 8 A shows the uniaxial tensile test results for PCL and PCLbisurea electrospun scaffolds along and perpendicular to (FIG. 8 B) the main fiber direction.

FIG. 9 B shows comparative results of conduit fatigue testing conducted using PCL bisurea and PCL UPy implants.

DETAILED DESCRIPTION

Figure 1:
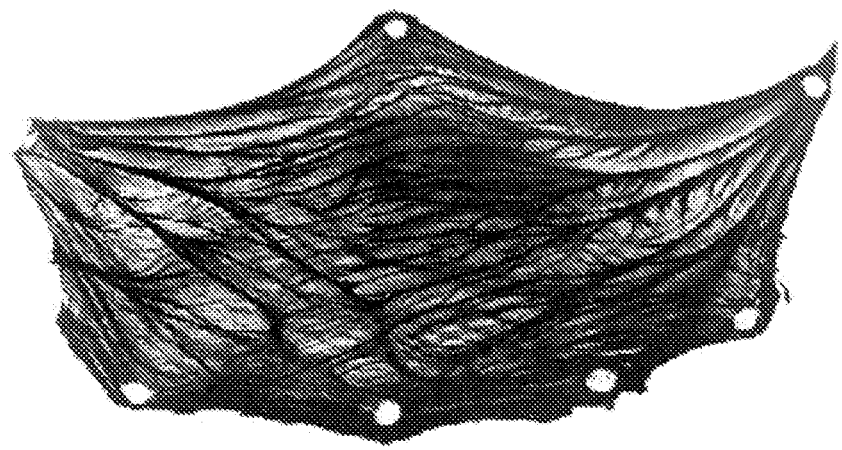
FIG. 1 shows native fiber orientations of a heart valve leaflet (Sauren (1981)).

In the present description and appended claims, the following terms are used, which are explained below.

A "polymer" is intended to also include homopolymer, copolymer or supramolecular polymer unless otherwise stated.

A "supramolecular polymer" is a polymeric array of monomeric units that are brought together by reversible and highly directional secondary interactions, resulting in polymeric properties in dilute and concentrated solutions, as well as in the bulk. The monomeric units of the supramolecular polymers themselves do not possess a repetition of chemical fragments. The directionality and strength of the supramolecular bonding are important features of these systems, that can be regarded as polymers and behave according to well-established theories of polymer physics.

A "supramolecular monomer compound" in this application is a compound which by virtue of reversible and highly directional secondary interactions (with other supramolecular monomer compounds) forms a supramolecular polymer.

A supramolecular polymer is therefore composed of monomers, which monomers are designed in such a way that they autonomously self-assemble into the desired polymeric structure. This is in contrast to conventional polymerization reactions whereby monomers are linked via covalent bonds. As a result of the self-assembly, a (much) higher virtual molecular mass of the material is achieved. Examples of supramolecular polymers have been described in, for example, Science, 1997, 278, 1601.

A "contrast agent" is a substance used to enhance the contrast of structures or fluids within the body in medical imaging.

A "scaffold" is a temporary structure used to support material (e.g. tissue) during the formation and/or recovery of said material.

A "structural component" is the part of the scaffold that is intended for the provision of structural properties.

An "imaging component" is the part of the scaffold that is intended for the provision of imaging properties.

A "biologically active component" is the part of the scaffold that is intended for the provisional of biological activity.

A "substrate" is the material on which growing of cells takes place.

An "implant" is a medical device that can replace a dysfunctional or damaged biological structure, support a damaged biological structure, cover a damaged biological structure, or enhance an existing biological structure.

"Backbone of a polymer" is the backbone chain (also called main chain) and is a series of covalently bonded atoms that together create the continuous chain of the polymer.

"Porosity" is measured, for example, by mercury porosimetry, fluid intrusion and gravimetry.

"Pore size" is the average size of openings (pores) in the matrix material. Porosity as mentioned in the specification is measured as follows:

The scaffold weight is measured using a balance. The dimensions (length and thickness for tubes, length, width and thickness for sheets) are also measured. The porosity is calculated using the following formula:

porosity=(1−Density of scaffold/density of polymer)×100% where density of polymer varies based on the polymer used and density of scaffold is calculated as weight of scaffold/volume of scaffold.

By "pores," it is meant the inter-fiber spaces (that is, the pore size) in the matrix material. The pore size and porosity are properties of a scaffold that influence the attachment, proliferation, migration and/or differentiation of cells.

A "minimally invasive procedure" is a procedure (surgical or otherwise) that is less invasive than open surgery.

The inventors have surprisingly found that the above object is reached with an implant comprising a matrix material having a porosity of at least 60%. Said implant can by implanted in a subject (also called recipient of the implant) with a minimally invasive procedure. Due to the porosity of at least 60%, the implant can be compressed minimizing the size of the implant (also referred to as crimping). Since the size of the implant is reduced, a smaller opening is required for implantation resulting in less discomfort to the recipient of the implant and minimizing recovery time of the recipient. Preferably, the porosity is between 70% and 90%. Further a fiber structure with such a porosity allows for diffusion of nutrients into the matrix and for the ingrowth and/or infiltration of cells into the matrix.

The inventors have found that they can solve one of the major limitations currently associated with minimal invasive implantation of e.g. prosthetic heart valves by allowing crimping to a smaller size compared to existing transcatheter heart valves.

In an embodiment of the present disclosure, the implant is a cardiovascular implant and preferably an implant chosen from the group consisting of a (blood) vessel, a heart valve, a cardiovascular patch or a valved conduit. It is beneficial for the recipient that an implant according to the present embodiment can be implanted by minimal invasive surgery. For these implants, only a minor incision has to be made in order to facilitate implantation. Preferably, the implant is applied to an object (i.e. a patient) via a small incision. Due to the high porosity of the implant the implant can be reduced at least 5 times in diameter size going from fully expanded towards fully crimped configuration and back.

In an embodiment of the present disclosure, the implant is reinforced by at least one support structure, preferably the at least one support structure is chosen from the group consisting of a reinforcement ring, a suture ring or a stent structure, and is preferably biodegradable, preferably the implant consists of the reinforced matrix material. The presence of the support structure can, for example, be aimed at reinforcing the implant, allowing crimping of the implant during a minimally invasive procedure, allowing fixation of the implant at the correct anatomical position or allowing repeated puncturing of the implant with a needle. Suitable support structures are those widely known in the art and are, for example, used in artificial heart valves or as coronary stents or stents for other kinds of arteries. Reinforcements are for example described in U.S. Pat. Nos. 4,626,255, 6,338,740, US 200410148018, U.S. Pat. Nos. 3,570,014 and 4,084,268.

In an embodiment of the present disclosure, the implant has a matrix material which consists of a fibrous network. Said fibrous network is made up out of fibers. The fibers allow for the implant to have good structural integrity while maintaining its porosity and pores. Preferably, the fibrous network are electro spun fibers. Electro-spinning is a technique using a metal target or mold, having either a flat, plate-like form or a complex three-dimensional form, depending of the preform that is desired. Polymer fibers are deposited onto this mold by means of an electromagnetic field. The polymer fibers are generated from a solution of one or more polymers in one or more solvents. This technique of electro-spinning is known in the art and will not be further in detail in this specification. In Dutch patent NL 1026076 (corresponding to US 2008/0131965), the preparation of an article by means of electro-spinning of polymer microfibers is disclosed. The electrospinning setup used in the development of such a product is climate controlled and also allows for control of spinning area, nozzle speed, rotation of the collector and the possibility of the applying a small negative voltage (up to −4 kV). The humidity, temperature and other above-mentioned factors can be used alone or in combination to alter various characteristics of the electrospun fibers. These include, but may not be limited to, fiber morphology, fiber diameter, fiber and pore size distribution, porosity and scaffold thickness.

In an embodiment of the present disclosure the fibers of the matrix material consists of one or more supramolecular polymers. By using these kinds of polymers, the inventors have found that the implant can be implanted in a subject without having to seed the implant with cells prior to implantation. By using supramolecular compounds, the inventors observed that cells attach, infiltrate and grow in vivo on and in the implant while the implant fulfills the function of the tissue to be replaced or repaired. Hence the implant can be implanted directly in the patient. The advantages of implanting a scaffold directly are a reduction in production time and cost, the scaffold can be stored for prolonged periods of time and it qualifies as a medical device meaning that regulatory approval can be obtained much faster. Hence, one or more of the important drawbacks of growing a tissue construct, or seeding cells, in vitro are overcome, while keeping the advantage and promise of regeneration, leaving only new healthy tissue behind.

In an embodiment of the present disclosure, the implant is biodegradable. This allows for the implant to be degraded after being implanted in the body. Hence the implant is replaced over time by tissue. The advantage is that the implant does not have to be removed surgically preventing further discomfort for the patient who received the implant.

The inventors found that if one or more supramolecular compounds have a backbone comprising or consisting of polycaprolactone (PCL) or a combination of PCL, caprolactone, poly lactic acid and/or lactic acid very good results are obtained with respect to the structural characteristics of the implant and with respect to biodegradability.

In an embodiment of the present disclosure, the implant has a matrix material that comprises one or more supramolecular compounds wherein the one or more supramolecular compounds further comprise one or more groups chosen from UPy (ureido-pyrimidinone) and/or bisurea. A polycaprolactone polymer containing UPy-groups, is for example disclosed in patent application EP 1 687 378. Preferably, the supramolecular compound is PCL-bisurea (also referred to as PCLbu). The present inventors have found that with these compounds good results can be obtained with respect to the in vivo growth of tissue in the implant as well as for structural characteristics of the implant. Good results are obtained with PCL-bisurea.

In an embodiment, the one or more supramolecular compounds comprises at least PCL UPy, preferably the matrix material consists of PCL UPy. Especially good results are obtained with PCL-UPy.

A method for preparing PCL bis urea can be found in, for example, "Biomaterials by the supramolecular control of nanofibers by E. Wisse ISBN: 978-90-386-1094-8 chapter 2. The chemical formula of PCL-bis urea with a butyl spacer is shown in the Formula I below. Alternatively, no spacer or another alkyl spacer, e.g a hexyl spacer can also be used. The PCL acts as a soft-block while urea groups make up the hard block. The hydrogen bonding between the hard blocks results in reversible physical links.

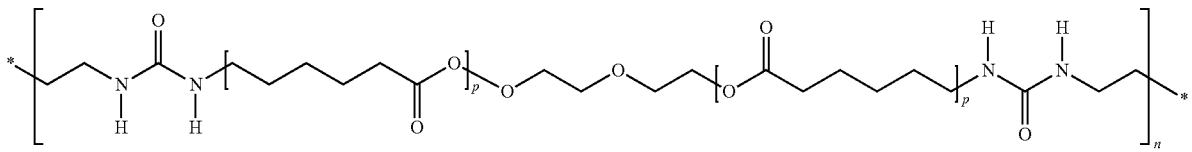

Formula I

10

Wherein p and n are integers and p and n>1. The p and n values can be altered to yield different formulations of PCL bis urea which might result in different properties. The p value is dependent on the starting molecular weight of polycaprolactonediol while the n value relates to the number of chain extensions of the PCL bis urea. Preferably values of n can range from 4-40.

A method for preparing PCL Upy can be found in, for example, "Biomaterials by the supramolecular control of nanofibers by E. Wisse ISBN: 978-90-386-1094-8 chapter 6. PCL-UPy polymers can be prepared, for example, as comprising the urea hydrogen bonding group (Upy-U 1) or the urethane hydrogen bonding group (UPy-U 2).

cells is generally larger than the size of animal cells, hence the differentiation between the most preferred pore sizes when using either animal or human cells.

In a preferred embodiment of the present disclosure, the matrix material forms a layer having a thickness of at least 100 .mu·m and maximally 3000 .mu·m, preferably the thickness is between 200 and 1000 .mu·m. In case the implant consists of matrix material, the implant has a thickness of at least 100 .mu·m and maximally 3000 .mu·m, preferably the thickness is between 200 and 1000 .mu·m. The inventors have found that with the defined thicknesses implants are obtained with good structural properties so that these implants can fulfill the desired function when

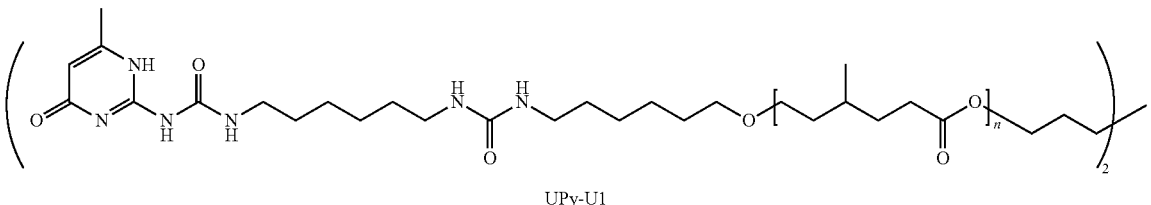

UPy-U1

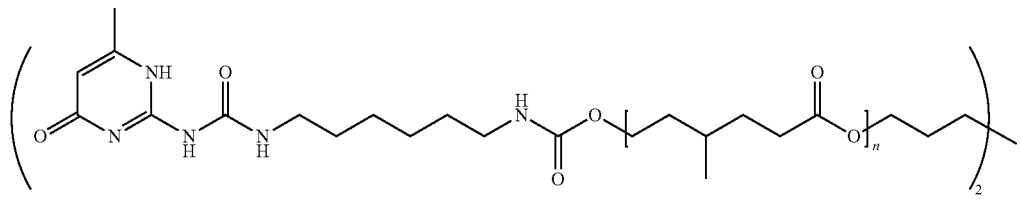

UPy-UT2

In an embodiment of the present disclosure, the fibrous network comprises nano fibers and/or micro fibers, preferably the diameter of the micro fibers ranges from 3 to 20 micrometers and preferably from 5 to 10 micrometers. The advantage of this diameter is the excellent mechanical and structural stability of the implant, while providing a microstructure that is sufficiently porous to allow for cell ingrowth (Balguid, Strategies to optimize engineered tissue towards native human aortic valves, PhD thesis Eindhoven University of Technology, 2008, ISBN 978-90-386-1185-3).

Nano fibers are fibers having a diameter of less 1 micrometer. The diameter of micro and nano fibers can be obtained by measuring the diameter under a microscope.

In an embodiment of the present disclosure, the matrix material comprises pores having a diameter ranging from 1-300 micrometer and preferably ranging from 5-100 micrometer. The advantage of these pore sizes is that it allows the passage of the cells to be cultured and hence a good infiltration of cells into the complete thickness of the preform, which is required to ensure formation of tissue throughout the complete preform. The requirements of the pore size depend on the size of the cells to be cultured and can be selected according to this size. The size of human implanted in a subject while resulting in tissue growth and obtaining tissue of good quality.

In an embodiment of the present disclosure, the implant has a linear elastic stiffness ranging from 0.1-50 MPa and preferably from 0.1-10 MPa. The inventors have found that these ranges provide the combination of strength and flexibility that is required to withstand the hemodynamics of the human cardiovascular system. Previously published results on native and tissue engineered materials report stiffness values in this range as well (Non-invasive assessment of leaflet deformation and mechanical properties in heart valve tissue engineering by Kortsmit, ISBN: 978-90-386-2002-2 (2009). Stradins et al. (2004), Clark, (1973)).

In an embodiment of the present disclosure, the implant has an (linear) elastic regime of at least 30%, and preferably at least 45% and more preferred at least 60% (Linear elastic stiffness has been measured using standard uniaxial tensile tests (for a description see ISO 13934-1:1999 Textiles—Tensile properties of fabrics—Part 1: Determination of maximum force and elongation at maximum force using the strip method)). This ensures that an implant according to the present embodiment does not show plastic deformation or breakage within a physiological strain region (strain exerted in the body on the implant). For example, for native heart valves, physiological strains have been reported of about 60% (Billiar & Sacks, (2000), Driessen et al., 2005)). Current bioprosthetic valves already fail to comply with these values, showing maximal strains during diastolic pressurization of gluteraldehyde treated porcine valves of 2-4% and 3-10% in circumferential and radial direction, respectively (Adamczyk & Vesely, 2002), and an average strain value of 4-10% in the heart valve leaflets (Sun et al., 2005). Furthermore, chemically fixed anisotropic tissue was described to become more isotropic (Zioupos et al., 1994) and less compliant than fresh tissue (Broom et al., 1982; Schoen et al., 1997; Billiar & Sacks, 2000) due to chemical crosslinking. Commercially available polymers that were shown to have a short elastic regime in a uniaxial tensile test, also showed insufficient performance in an in vitro valve testing set-up. Thus, for the implant to be used in the body and fulfill the function of the tissue to be replaced or repaired an extended elastic regime is important.

In an embodiment of the present disclosure, the implant, the fibers (of the matrix material) have a preferred orientation direction. Preferably, the fibers in the implant are arranged in such a way that when the implant is implanted, the fibers are arranged substantially perpendicular to the blood stream.

Preferably, the preferred fiber alignment is circumferential around an imaginary axis of the implant wherein the axis points in the direction of bloodflow in case of a tubular implant. In case of a heart valve leaflet, the fibers are preferably arranged in the same fashion as depicted in FIG. 1.

Figure 2:
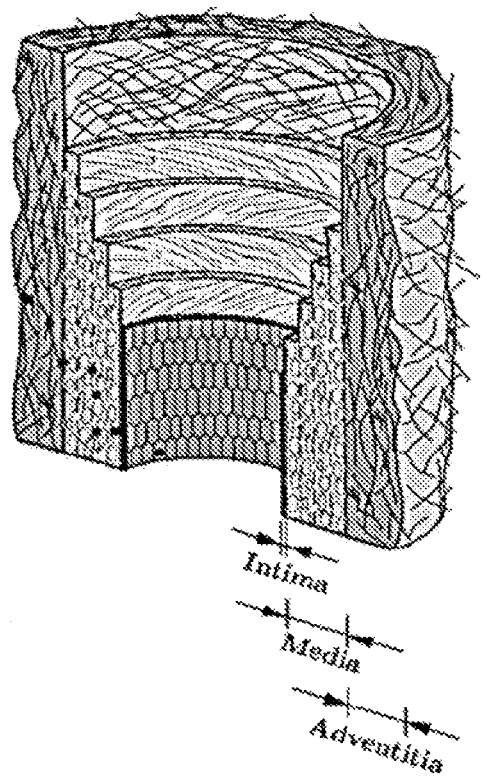
FIG. 2 shows helical fiber orientation in blood vessel (Holzapfel, J. Elast., 2000).

Such an orientation can be introduced during manufacturing of the implant (i.e. with electro spinning). Such a fiber structure mimics the natural fiber alignment in native tissues, e.g. the hammock-like collagen architecture in native heart valve (as depicted in FIG. 1. Sauren et al. 1981) and the helical collagen fiber orientation in native arteries (as depicted in FIG. 2, by Holzapfel (2000))

By mimicking the extra cellular matrix of the natural environment, a tissue can be grown having good structural properties, which eventually develop towards a native-like architecture.

In an embodiment of the present disclosure, the linear elastic stiffness ratio between the stiffness in the preferred fiber direction and the stiffness perpendicular to the preferred fiber direction is at least 2:1, preferably at least 4:1 and more preferred at least 10:1 and even more preferred at least 50:1. Implants having such a ratio have good structural properties while still providing for a substrate for cells to grow on mimicking the natural environment.

In an embodiment of the present disclosure, the implant further comprises biologically active compounds and/or contrast agent. In order to monitor how fast the in vivo degradation of the implant proceeds, and in order to judge the ultimate success of the tissue engineering procedure, a contrast agent can be present in the implant. Said contrast agent can be visible in relevant clinical imaging techniques, such as computed tomography (CT), magnetic resonance imaging (MRI) and/or diagnostic sonography (or ultrasonography) using ultrasound for imaging purposes, for example. A preferred contrast agent is described in European patent application having application Ser. No. 10/193,654, a fluorinated polymer having a glass transition temperature (Tg) below 40 degrees Celsius, preferably below 20 degrees Celsius, more preferably below 0 degrees Celsius, as an imaging label or contrast agent in 19F magnetic resonance imaging (MRI). The amount of fluorine (19F) in the fluorinated polymer is preferably at least 5 wt %, based on the total mass of the polymer. Said fluorinated polymer comprises at least one polymer selected from the group consisting of (per)fluorinated polyethers, (per)fluorinated polyesters, (per)fluorinated poly(meth)acrylates, and (per)fluorinated polysilicones, preferably (per)fluoroethers. Said polymers can be incorporated in the polymers making up the fibrous network. Alternatively, the polymers are present separately in the fibrous network.

Biological active compounds can be added to, for example, promote cell infiltration, retainment, differentiation and proliferation, as well as tissue formation and remodeling.

The present disclosure further relates to a method for manufacturing an implant, preferably as described above, having a matrix material one or more supramolecular compounds, wherein the matrix material has 60% porosity and preferably between 70 and 90% porosity, comprising the steps of:

Providing a mold;
Applying the matrix material to the mold by means of electro spinning of one or more supramolecular compounds; and
Separating the matrix material from said mold.

The obtained implant has the same advantages as described above. In an embodiment of the present disclosure, the method further comprises the step of providing at least one support structure to the implant or matrix material.

The disclosure further relates to a crimped implant, preferably the implant according to embodiments as previously described, which can be crimped to a diameter size of up to 20% compared to the diameter of the implant before crimping (uncrimped). This allows for the implant to be easily provided by minimal invasive surgery. A further advantage is that since the implant can be crimped to 20% of its initial diameter size, it can be provided to subjects that currently are excluded from receiving an implant via minimal invasive surgery because, for example, their arteries are too narrow for a crimped implant according to the prior art to pass through. Preferably, the crimped implant is a heart valve implant. Crimping an implant according to the present disclosure is achieved by methods known in the art. An example of crimping is given in the examples.

The present disclosure further relates to a method for growing a valve, comprising the step of providing an implant, preferably an implant according to the present disclosure to a subject (a patient). The implant is preferably an implant according to the present disclosure. This step can be preceded by the step of making an incision in the skin of the subject.

After implanting the implant in the patient (human or animal) the implant is capable of functioning (as the tissue to be grown) after implantation and before cellular ingrowth occurs, and wherein cellular ingrowth occurs after implantation and the matrix material is degraded over time.

The embodiments will be further illustrated by the following non limiting examples. The appended claims also form part of the description of the present application.

EXAMPLES

Example 1

Figure 14:
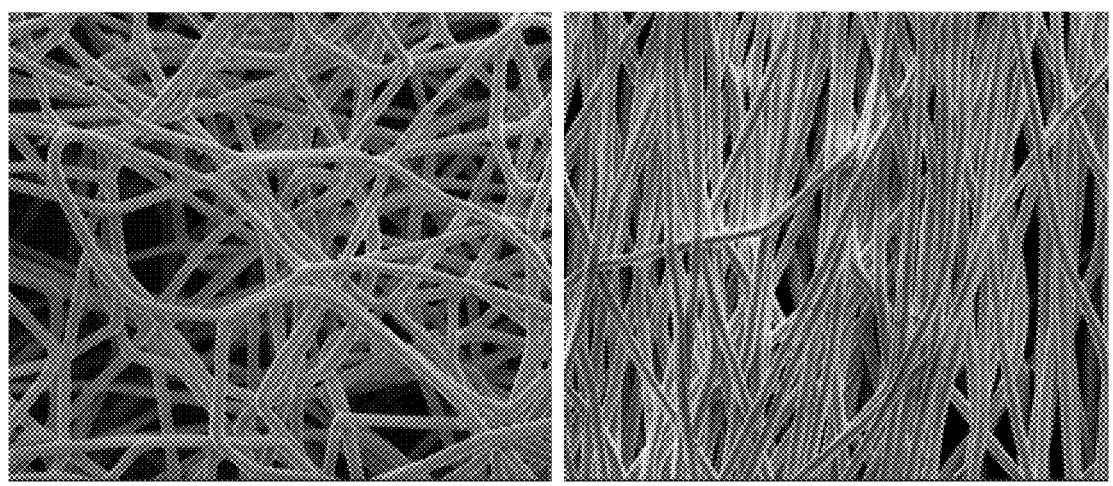
FIG. 14 shows two SEM images of PCL and PCL-bisurea matrices.

Implants were manufactured according to the following method. A required amount of PCL, PCL bisurea or PCL UPy is dissolved in an appropriate solvent/solvent mixture and stirred until dissolution. The resulting solution is delivered at a constant flow rate (flows varying with time are also possible and will result in scaffolds with different properties) to a nozzle that can be electrically charged. Typically, this is done using a syringe pump. A high voltage is applied to the nozzle. Voltage differences (combination of positive and negative voltages) used range from 10-20 kV, although it is possible to produce fibers at other voltages. A rotating collector, usually in the form of a cylinder is placed. The collector is connected to the ground or a negative terminal. The speed of rotation is typically 100 rpm. The fibers are deposited on the collector. The length and thickness of the produced implant is affected by flow, voltage, collector rotation speed, sweep and the nozzle speed. After the desired thickness is achieved, the spinning is stopped and the collector is removed. The implant in the collector is vacuum dried and annealed (about 37 degrees Celsius) overnight. The implant is removed by the collector by soaking it in warm water (about 37 degrees Celsius), although other methods of removal are possible. A SEM image of an electrospun fiber mesh is shown in FIG. 14.

Example 2

Figure 7:
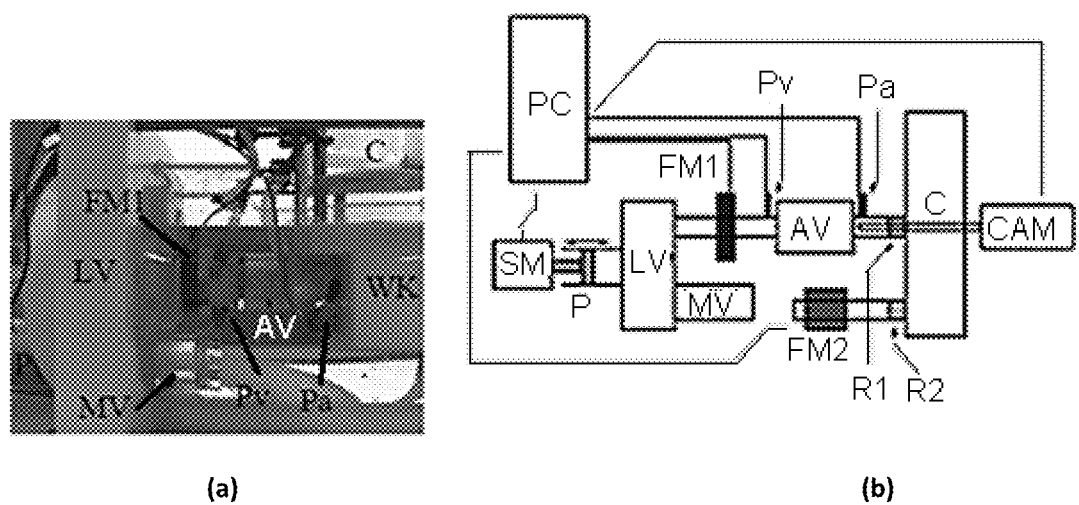
FIG. 7 shows Photograph (a) and schematic overview (b) of set-up for valve testing.

The implants obtained according to the method of example 1 were tested in accordance with ISO5840:2005. The hemodynamic performance of a valvular implant is assessed by loading with physiologically relevant flow and pressures by means of a mock loop system. FIG. 7 shows an image of the mock loop used. The valves to be mounted in this mock loop are subjected either to pulmonary pressures and flow or to aortic pressures and flow. The fluid used in the experiments is a physiological saline solution. In the mock loop system shown above, the circulation fluid is displaced by means of a computer (PC) controlled piston pump (P). The piston is connected to a servomotor (SM) system that is controlled by a motion control board. The piston fills the left ventricular cavity (LV; VLV=1 L) from a reservoir through a model mitral valve (MV) and subsequently ejects the fluid through the arterial valve (AV) into a WindKessel (WK) model that consists of two resistances (R1 and R2) and a compliance tank (C; VC=2 L). From the Windkessel model, the fluid flows back into the reservoir through a section of silicone tubing. The pulsatile flow through the arterial valve is measured by a Flow Meter (FM1). Additionally, the mean Cardiac Output is registered by means of a Clamp-On flow sensor (FM2) on the outlet silicon tube of the WindKessel. Ventricular and arterial pressure is recorded using pressure transducers (Pv and Pa) that are connected to a bridge amplifier (Picas. Peekel Instruments). The signals are recorded by a Data-Acquisition board and stored on a hard disk in a PC. An endoscope is introduced into the systemic artery to which a high-speed color camera is connected (M5) to capture valve dynamics throughout the heart cycle at a frame rate of 200 Hz. Valvular pressure and flows are monitored over time to assess valve functionality.

Figure 3:
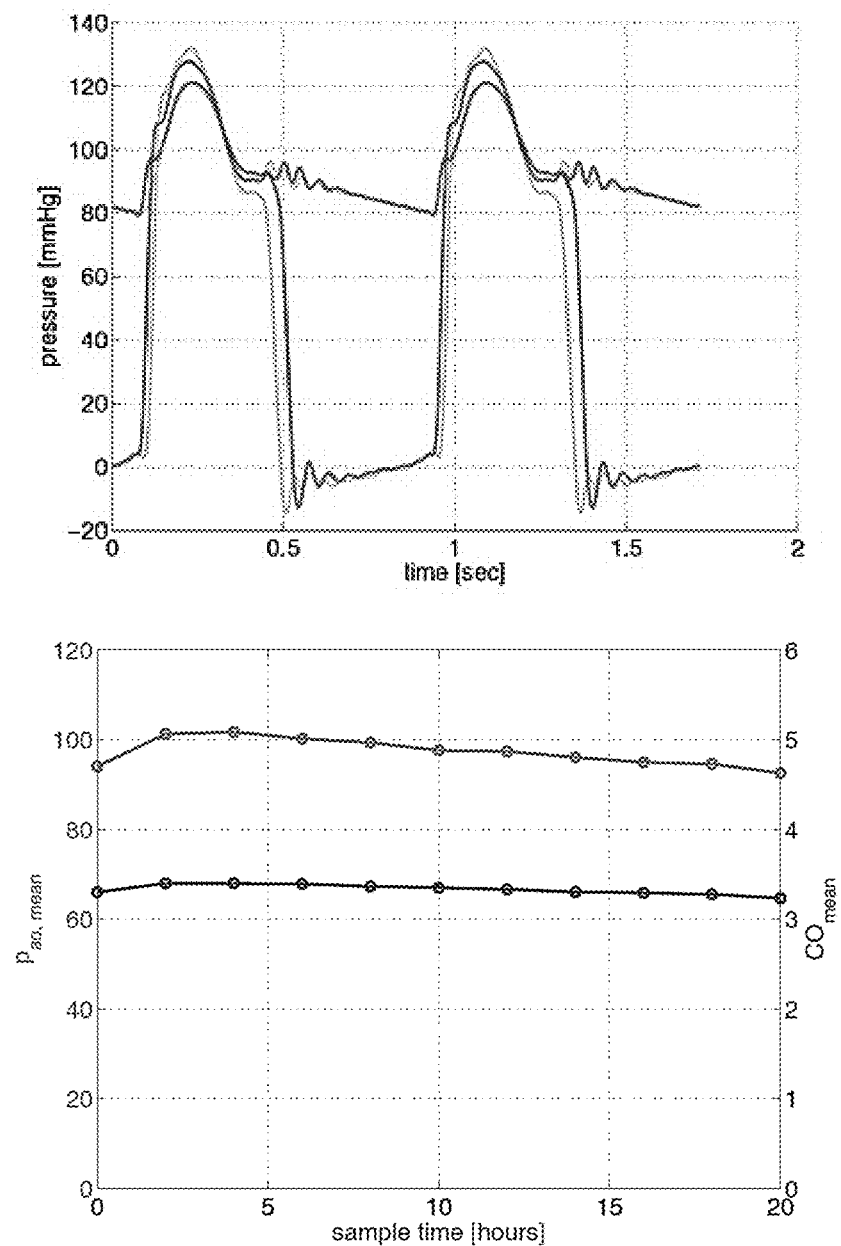
FIG. 3 shows results of valve testing at 120/80 mmHg on a PCL-bisurea valve at systemic conditions showing stable performance for 20 hours.

Valves made from PCLbu and PCL were subjected to systemic conditions at 120/80 mmHg for 20 hours. The obtained results clearly show better results for PCLbu (FIGS. 3 and 4) implants than for PCL implants (FIGS. 5 and 6).

Figure 4:
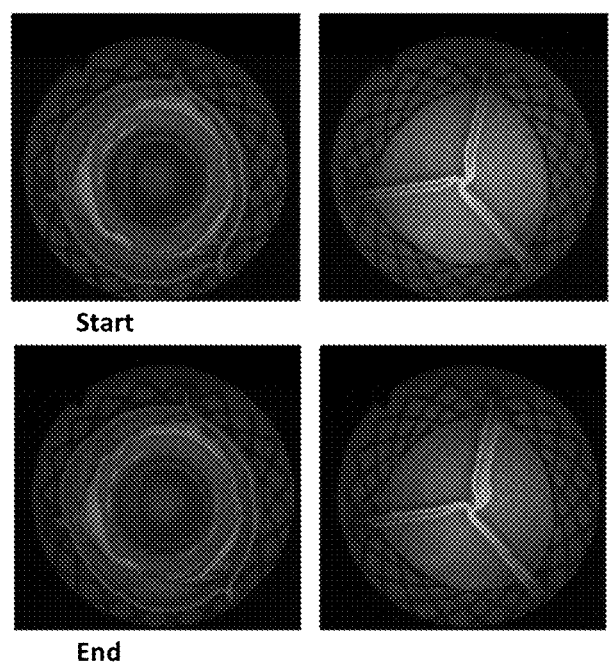
FIG. 4 shows pictures of PCL-bisurea valves at start (two upper pictures) and after 20 hours (two lower pictures) of systemic conditions in a valve test, 20 hours (R11020).
Figure 5:
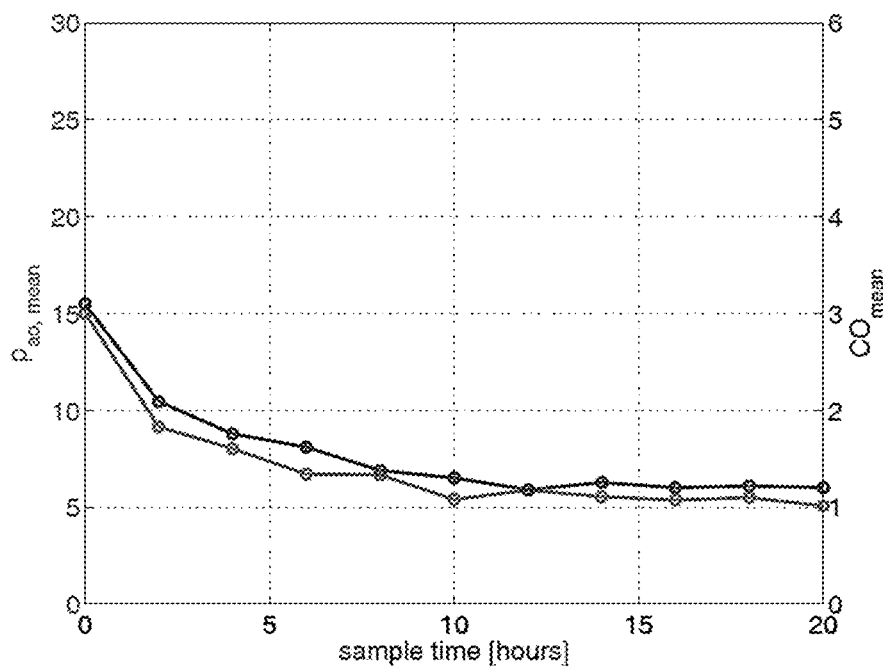
FIG. 5 shows results of valve testing at 50/25 mmHg on a PCL valve at systemic conditions showing a decreasing in performance within several hours.
Figure 6:
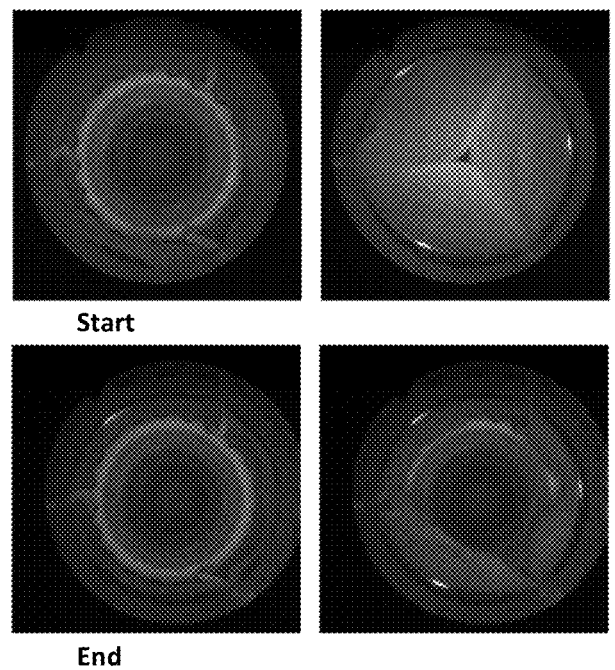
FIG. 6 shows pictures of PCL valves at start (two upper pictures) and after 20 hours (two lower pictures) at 50/25 mmHg in a valve test, 20 hours (R11020).

The pictures of FIGS. 4 and 6 show a valve in the opened (left top picture) and closed (right top picture) configuration at the start of the test and in the opened (left bottom picture) and closed (right bottom picture) after 20 hours. The pictures of the tested valves clearly show that the PCL valves are damaged whereas the PCLbu valves remained largely undamaged.

Example 3

Uniaxial Tensile Test

The Zwick tensile stage is connected to a measurement module, which is connected to a PC. After the necessary preparations, this system can be used to retrieve the stress-strain characteristics of strips of for example biological tissue. First, both sides of the sample are mounted in the tensile stage with the use of the two clamps. Software on the PC triggers the tensile stage, thereby elongating the sample. During this elongation, displacement, as well as force, is recorded, and subsequently stored in an TRA file. From this file, complemented with the dimensions of the specimen, mechanical parameters (Young's Modulus, ultimate tensile strength/strain) can be determined using Matlab. RT (dry), grip-to-grip separation=9 mm, elongation rate=9 mm/min, 20N load cell.

Width and thickness are used to calculate the Young's Modulus [Pa], which is a measure for the stiffness of the strips.

$$E = \frac{F_2 l_2 - F_1 l_1}{(l_2 - l_1) A_0} \tag{Eq. 1}$$

F [N] is the force and l [m] the length of the sample (length [mm]*$10^{-3}$).

A0 [($m^2$)] denotes the cross-sectional area of the sample before testing (width [mm]*thickness [mm]*$10^{-8}$).

FIG. 8 A shows uniaxial tensile test results for PCL and PCL-bisurea electrospun scaffolds along (left) and perpendicular to (right) (FIG. 8 B) the main fiber direction, showing a clear difference in elastic regime (straight line) between the 2 materials. For PCL plastic deformation around 10% strain and breakage observed below 15% strain (perpendicular). For PCL-bisurea, no plastic deformation or breakage within physiological strain region (<60%) was observed under the same conditions.

Example 4

Fatigue Testing
A) Uniaxial Fatigue Test

Figure 9:
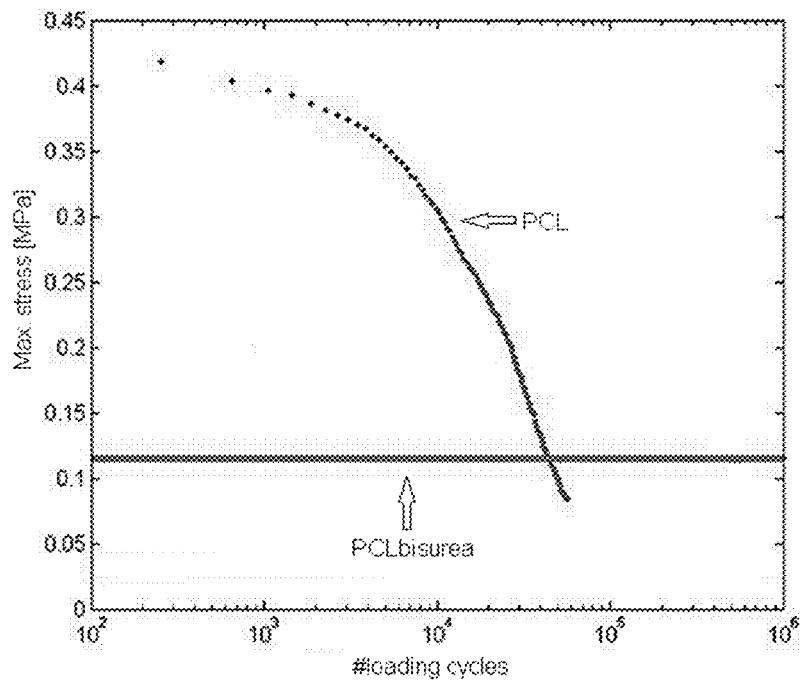
FIG. 9 A shows the results of the uniaxial fatigue tests (10%, 2 Hz) on PCL and PCLbisurea.
Figure 9:
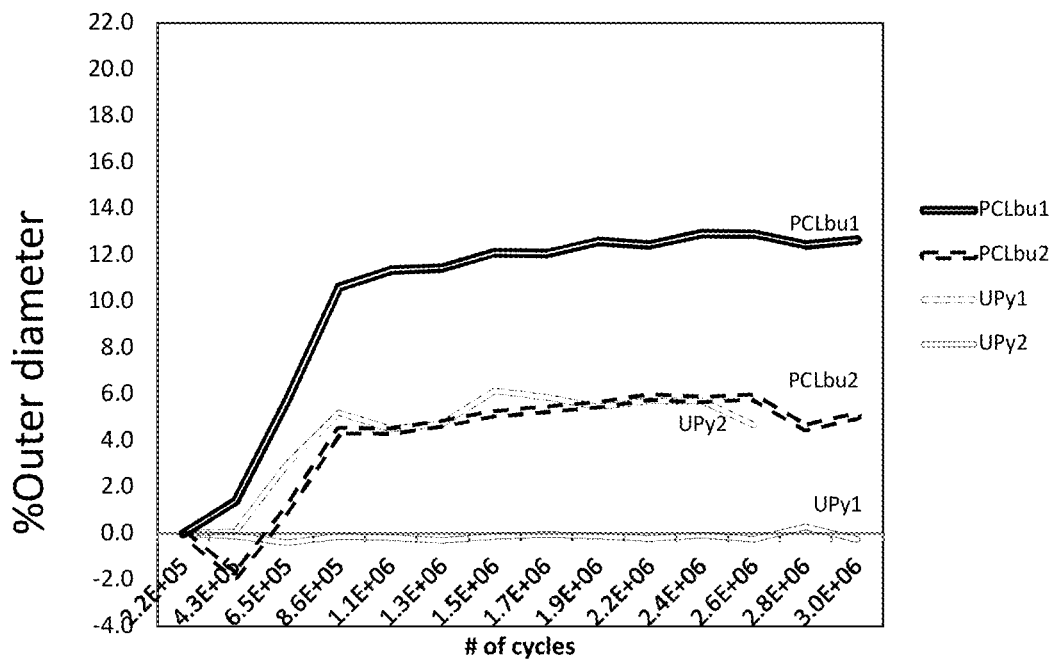

Using a set-up similar to the uniaxial tensile test, cyclic loading was performed to assess the fatigue behavior in a uniaxial fatigue tests (10% strain, 2 Hz) on PCL and PCLbisurea. Results confirm failure modes and timelines observed in the valve test (Example 2), showing fatigue within 1000 cycles (<% hour in-vivo) for valves made from PCL, and no fatigue for valves made from PCL-bisurea. Even after 1 million cycles (>11 days in-vivo) no fatigue damage was observed for the PCLbisurea valves (FIG. 9 A).
B) Conduit Fatigue Test The implants obtained according to the method of example 1 were tested for fatigue resistance by applying cyclic pressure loads to tubular shaped scaffolds. This benchtop test is used to determine the durability of a vascular device by subjecting it to hydrodynamic pulsatile loading with a relevant pressure differential. Device specimens are submerged in an environmental chamber and fatigued for 3 million cycles. Test conditions are designed to meet the requirements of in vitro mechanical fatigue testing stated in ASTM F 2477-07 "Standard Test Methods for in vitro Pulsatile Durability Testing of Vascular Devices" and FDA Guidance 1545 (2010) "Non-Clinical Engineering Tests and Recommended Labeling for Intravascular Devices and Associated Delivery Systems". The test is controlled and monitored via the pressure control method, which dictates that the test will control the cycle pressure range within desired ranges. The frequency was set to 5 Hz, temperature to 37 degrees Celsius, and the pressure ranges were set at 35/15 mmHg. As output, the outer diameter of the tested scaffold is measured as a function of the amount of cycles.

FIG. 9B clearly shows that PCLbu based materials have a higher increase in outer diameter as a function of amount of cycles when compared to UPy materials, indicating that UPy materials are even more resistant to fatigue failure. Comparing the results from shown in FIG. 9 A with FIG. 9 B it is clear to see that the PCL-bisurea withstands fatigue better PCL implants and furthermore PCL-UPy implants withstand fatigue even better then PCL-bisurea implants.

FIG. 15 also shows results for 2 different PCLbu configurations and 2 different UPy configurations, which demonstrates that by tuning the scaffold material, the fatigue properties can be improved for PCLbu as well as UPy based scaffolds Example 5

Youngs modulus for isotropic and anisotropic electrospun PCLbu strips were obtained from which the stiffness ratios were calculated. The results are listed in Table 1.

TABLE 1

| 1-6% strain | Initial Youngs modulus [MPa] | | |
|---|---|---|---|
| n = 3 | Parallel | Perpendicular | Ratio |
| Isotropic | 5.1 ± 0.29 | 4.2 ± 0.23 | 1.2:1 |
| Anisotropic | 31 ± 4.0 | 0.60 ± 0.10 | 52:1 |

Table 1 clearly shows that anisotropic spun PCLbu strips show a high Young modulus when measured parallel to the preferred orientation of the fibers and a low Young modulus when measured perpendicular to the preferred fiber orientation. Table 1 shows that for isotropic spun PCLbu strips the Young modulus measured in the parallel direction is comparable to the Young modulus in the perpendicular direction.

Example 6

Crimping Test

Figure 10:
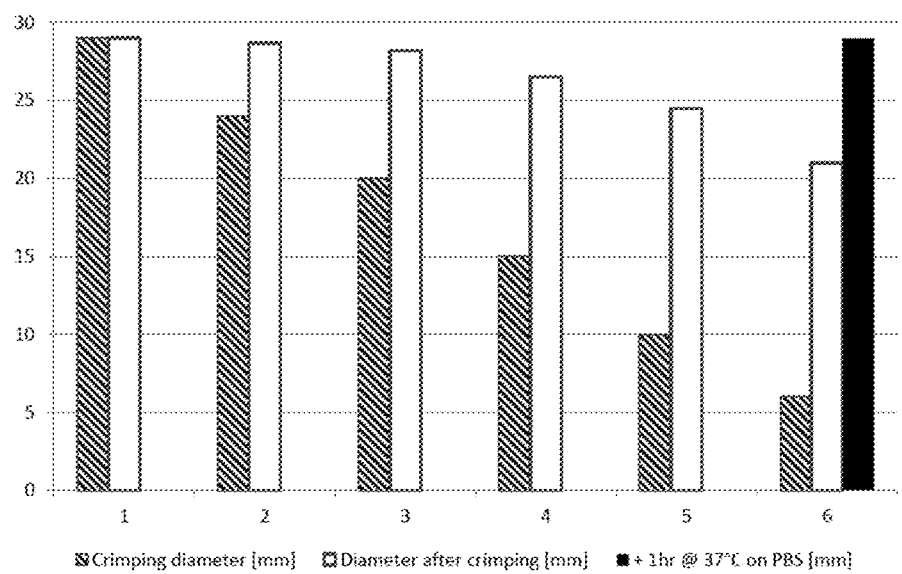
FIG. 10 shows the results of the crimping tests on electrospun heart valve implants.
Figure 11:
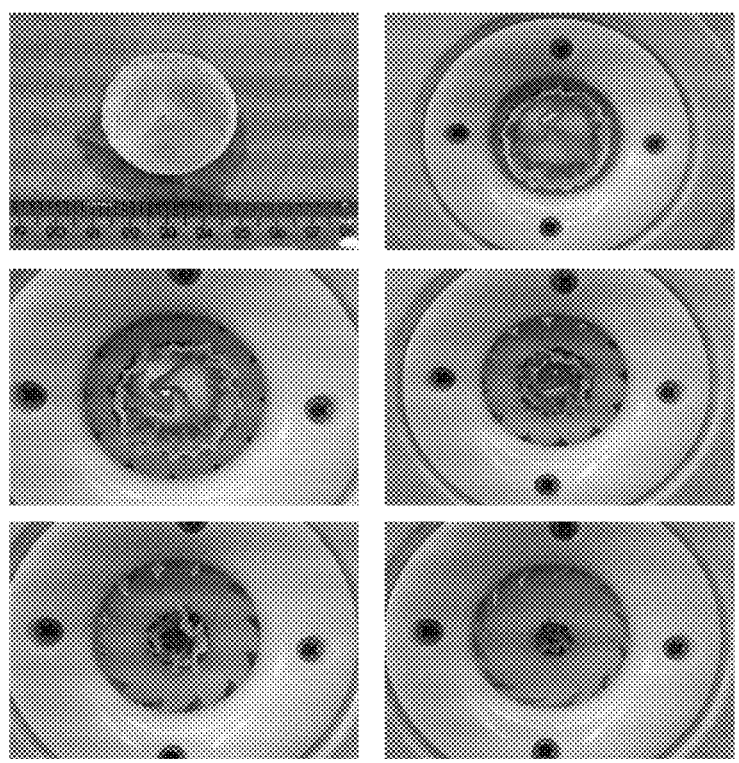
FIG. 11 shows the different crimped states of 3D electrospun heart valves.

Implants according to the present embodiment having a diameter of 28 mm were subjected to a crimping test. The implants were shrunk to a certain diameter using a commercially available device for crimping transcatheter heart valves. The different stages of the crimping process are depicted in FIG. 11. After that, they were allowed to return to their normal size. After unfolding, the diameters were measured again. The results are shown in FIG. 10 wherein the striped bars represent the diameter to which the implant is crimped, the white bar represents the diameter of the implant after it has been allowed to return to its uncrimped size and the black bar represents the same as the white bar but after soaking the implant in PBS at 37 degrees Celsius for 1 hour.

Figure 12:
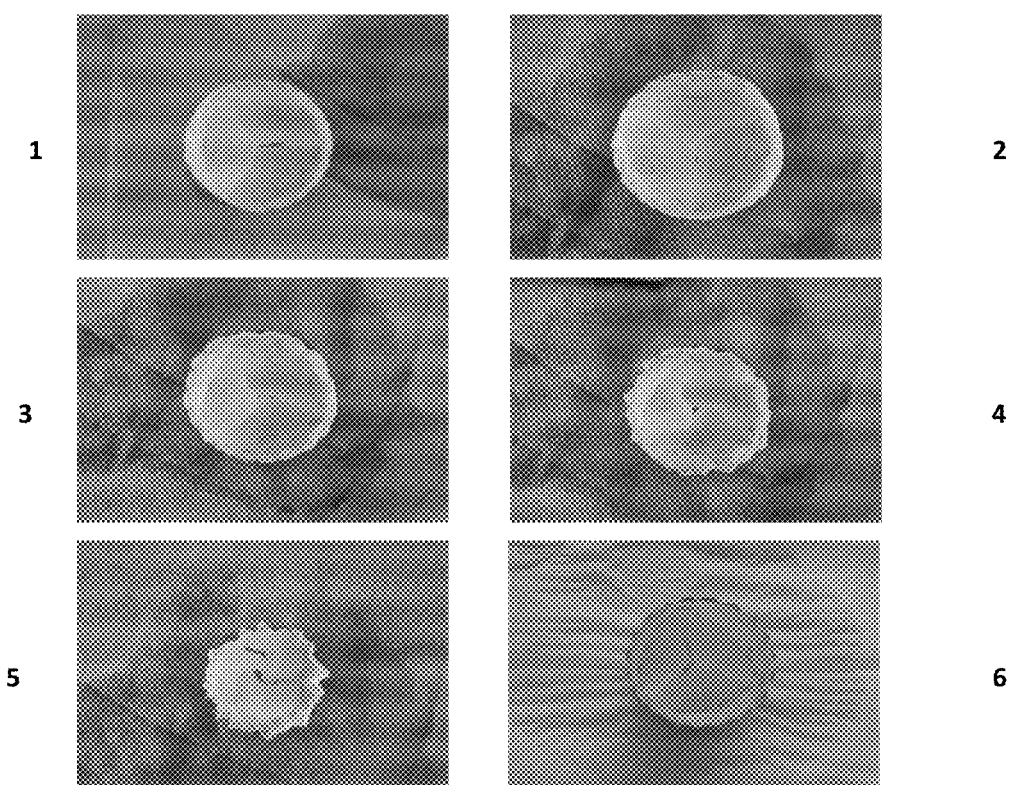
FIG. 12 shows the stents after different stages of crimping for 30 electrospun heart valves.

From the results, it is clear that even after the implant has been crimped to a diameter of 8 mm, return to its initial size (diameter of 29 mm) was still observed after soaking in PBS at 37 degrees Celsius for 1 hour. FIG. 12 shows pictures of the valves after being allowed to return to their uncrimped size. The numbers next to the picture correspond to the numbers of FIG. 10.

Example 7

In Vivo Testing

Figure 13:
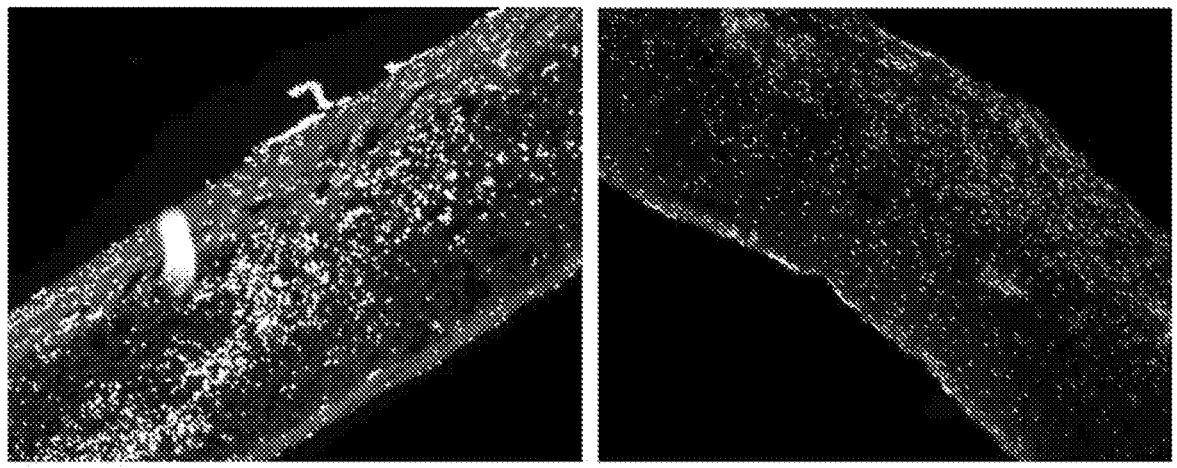
FIG. 13 shows three pictures of DAPI staining of a PCL-bisurea implant in an ovine model.
Figure 13:
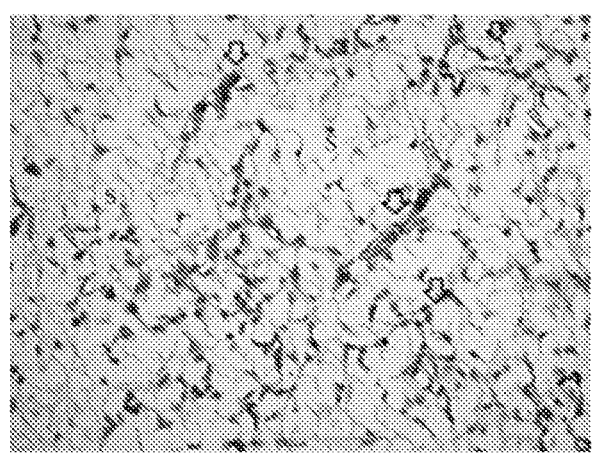

An implant according to the present embodiment was implanted at the pulmonary valve position in an adult sheep using open heart surgery. Cells were visualized with DAPI staining and cell infiltration was assessed under a microscope. Cell infiltration was assessed 1 day, 7 days and 8 weeks after implantation. The results are depicted in FIG. 13. The upper left picture shows cell infiltration after 1 day and the upper right picture after 7 days for the PCLbisurea implant and the lower picture shows cell infiltration in the PCL-UPy implant after 8 weeks. The pictures clearly show that cells in vivo infiltrate the PCLbisurea implant and the PCL-UPy implant.

What is claimed is:

1. A crimped cardiovascular implant for regenerating tissue in vivo, comprising: at least one support structure and a fibrous network consisting of one or more polymer compounds, wherein the fibrous network has at least 60% porosity pores with a diameter ranging from 1 to 300 micrometers, and a linear elastic stiffness ranging from 0.1 to 50 MPa, and wherein the implant is free of cells prior to implantation.

2. The crimped cardiovascular implant as set forth in claim 1, wherein the crimped cardiovascular implant has a diameter size which is 20% or less compared to the diameter of the uncrimped implant.

3. The crimped cardiovascular implant as set forth in claim 1, wherein the porosity is between 70% and 90%.

4. The crimped cardiovascular implant as set forth in claim 1, wherein the fibrous network is electrospun.

5. The crimped cardiovascular implant as set forth in claim 1, wherein the linear elastic stiffness ranges from 0.1 to 10 MPa.

6. The crimped cardiovascular implant as set forth in claim 1, wherein the implant is a blood vessel, a heart valve, a cardiovascular patch, or a valved conduit.

7. The crimped cardiovascular implant as set forth in claim 1, wherein the at least one support structure is a reinforcement ring, a suture ring, or a stent structure.

8. The crimped cardiovascular implant as set forth in claim 1, wherein the fibrous network is biodegradable.

9. The crimped cardiovascular implant as set forth in claim 1, wherein the polymer compounds are supramolecular compounds.

10. The crimped cardiovascular implant as set forth in claim 1, wherein the polymer compounds are supramolecular compounds with a backbone of polycaprolactone (PCL) or any combination of PCL, caprolactone, poly lactic acid, or lactic acid.

11. The crimped cardiovascular implant as set forth in claim 1, wherein the polymer compounds comprise UPy (ureido-pyrimidinone), bisurea or a combination thereof.

12. The crimped cardiovascular implant as set forth in claim 1, wherein the polymer compounds are supramolecular compounds comprising at least PCL UPy.

13. The crimped cardiovascular implant as set forth in claim 1, wherein the fibrous network has nanofibers, micro fibers, or a combination thereof.

14. The crimped cardiovascular implant as set forth in claim 1, wherein the pores having a diameter ranging from 5 to 100 micrometers.

15. The crimped cardiovascular implant as set forth in claim 1, having a linear elastic regime of at least 30%, and preferably at least 45% and more preferred at least 60%.

16. The crimped cardiovascular implant as set forth in claim 1, wherein the fiber alignment of the fibrous network is circumferential.

17. The crimped cardiovascular implant as set forth in claim 1, wherein the linear elastic stiffness ratio between the fiber direction and perpendicular to the fiber direction is at least 2:1.

18. The crimped cardiovascular implant as set forth in claim 1, wherein the crimped cardiovascular implant further comprises one or more biologically active compounds, one or more contrast agents, or a combination thereof.

19. A method for manufacturing a crimped implant by crimping a cardiovascular implant for regenerating tissue in vivo having at least one support structure and a fibrous network consisting of one or more polymer compounds, wherein the fibrous network has at least 60% porosity, pores with a diameter ranging from 1 to 300 micrometers, and a linear elastic stiffness ranging from 0.1 to 50 MPa, comprising the steps of:

providing at least one support structure;

providing a mold;

applying the fibrous network to the mold by means of electro spinning of the one or more polymer compounds to obtain an implant; and separating the implant and mold.

20. A crimped cardiovascular implant for regenerating tissue in vivo, comprising: at least one support structure and a fibrous network consisting of one or more polymer compounds, wherein the fibrous network has porosity between 70% and 90%, pores with a diameter ranging from 1 to 300 micrometers, and a linear elastic stiffness ranging from 0.1 to 50 MPa.

21. A crimped cardiovascular implant for regenerating tissue in vivo, comprising: at least one support structure and a fibrous network consisting of one or more polymer compounds, wherein the fibrous network has at least 60% porosity, pores with a diameter ranging from 1 to 300 micrometers, and a linear elastic stiffness ranging from 0.1 to 50 MPa, and wherein the fiber alignment of the fibrous network is circumferential.

* * * * *